US008562625B2

(12) United States Patent
Ding

(10) Patent No.: US 8,562,625 B2
(45) Date of Patent: Oct. 22, 2013

(54) METHOD AND APPARATUS FOR BREAKING UP CALCULI IN URINARY INTRACAVITY BY MILLING

(75) Inventor: Qiwu Ding, Guangxi (CN)

(73) Assignee: Qiwu Dang, Guangxi (CN)

( * ) Notice: Subject to any disclaimer, the term of this patent is extended or adjusted under 35 U.S.C. 154(b) by 126 days.

(21) Appl. No.: 13/122,609

(22) PCT Filed: Sep. 29, 2009

(86) PCT No.: PCT/CN2009/001108
§ 371 (c)(1),
(2), (4) Date: Jun. 22, 2011

(87) PCT Pub. No.: WO2010/040276
PCT Pub. Date: Apr. 15, 2010

(65) Prior Publication Data
US 2011/0251623 A1    Oct. 13, 2011

(30) Foreign Application Priority Data
Oct. 6, 2008    (CN) .......................... 2008 1 0073823

(51) Int. Cl.
*A61B 17/22* (2006.01)
(52) U.S. Cl.
USPC ........................................................ 606/128
(58) Field of Classification Search
USPC .......................... 606/127, 128, 159, 110–115
See application file for complete search history.

(56) References Cited

U.S. PATENT DOCUMENTS

| | | | |
|---|---|---|---|
| 4,899,733 A | 2/1990 | DeCastro et al. | 128/7 |
| RE35,787 E * | 5/1998 | Nash et al. | 606/128 |
| 6,475,225 B1 * | 11/2002 | Wulfman et al. | 606/159 |
| 2006/0229659 A1 * | 10/2006 | Gifford et al. | 606/200 |
| 2007/0037119 A1 | 2/2007 | Pal et al. | 433/119 |

FOREIGN PATENT DOCUMENTS

| | | |
|---|---|---|
| CN | 86200636 | 3/1987 |
| CN | 2476251 | 2/2002 |
| CN | 1756512 | 4/2006 |
| CN | 101380244 | 3/2009 |
| CN | 201260683 | 6/2009 |

OTHER PUBLICATIONS

International Search Report from PCT/CN2009/001108 filed Sep. 29, 2009; 4 pages.
Written Opinion for PCT/CN2009/001108 in Chinese; Date Jan. 7, 2010; 6 pages.

* cited by examiner

*Primary Examiner* — Ryan Severson
*Assistant Examiner* — Anh Dang
(74) *Attorney, Agent, or Firm* — Westman, Champlin & Koehler, P.A.

(57) ABSTRACT

The present invention discloses calculi breakup method and apparatus. The method comprises: inserting a combination of an endoscope with a driving assembly and a milling assembly, or a combination of an endoscope and a sleeve with a driving assembly and a milling assembly into the urinary intracavity; starting up a driving unit to drive the milling assembly so as to mill the calculi in the intracavity into powder; and, discharging the milled calculi powder out of the body. Compared to the other calculi breakup method, the calculi breakup apparatus according to the present invention has the advantages of high calculi breakup speed, high efficiency, no heat during the calculi breakup, no hurt to the urinary mucous membrane, painless, short time for the treatment, low calculi residual rate, simple operation, and easy maintenance.

7 Claims, 3 Drawing Sheets

METHOD AND APPARATUS FOR BREAKING UP CALCULI IN URINARY INTRACAVITY BY MILLING

CROSS-REFERENCE TO RELATED APPLICATION

This Application is a Section 371 National Stage Application of International Application No. PCT/CN2009/001108, filed 29 Sep. 2009 and published as WO2010/040276 on 15 Apr. 2010, in Chinese, the contents of which are hereby incorporated by reference in their entirety.

BACKGROUND OF THE INVENTION

1. Field of the Invention

The present invention relates to a medical apparatus, and in particular, it relates to a method and an apparatus for breaking up calculi in urinary intracavity.

2. Description of the Related Art

Calculi in a urinary system usually include renal calculus, ureter calculus, bladder calculus and urethra calculus, which belongs to a frequently encountered disease and a commonly encountered disease. There are several methods to treat calculi in the urinary system, such as, pharmaceutical treatment, treatment of calculi with extracorporeal shock wave lithotripsy, open operation for treatment, lithotrity treatment of calculi with the endoscope which are adapted to specific symptom of the diseases. With the development of the lithotrity treatment of calculi with the endoscope, it is increasingly adopted to treat a good variety of symptoms of the disease. There are a number of methods for treating the calculi with the endoscope, such as electrohydraulic shockwave lithotripsy, pneumatic ballistic lithotripsy, laser lithotripsy, ultrasonic lithotripsy, etc. However, the electrohydraulic shockwave lithotripsy falls into disuse due to its low speed and poor efficiency. Pneumatic ballistic lithotripsy and laser lithotripsy have the disadvantages of generating bulky stone fragments, picking up the stone fragments by repeated water flush or by a jaw during the operation, owning a relatively slow operation process, and easily causing residual stone fragments. Ultrasonic lithotripsy usually has a risk of massive hemorrhage because it requires a broad passage (of usually lager than 22F), furthermore, to adamantine calculi, the ultrasonic lithotripsy has an extraordinary low lithotripsy speed and efficiency and even encounters failure.

SUMMARY OF THE INVENTION

Accordingly, it is an object of the present invention to provide method and apparatus for safely breaking up calculi in urinary intracavity, which enable fast lithotripsy of renal calculus, ureter calculus, bladder calculus and urethra calculus. The method and apparatus of the present invention owns the advantages of high operation speed and efficiency, little residual stone fragments, and minimized damages to body tissues. Further, the present invention can not only be applied on the milling of the hepatic and gallbladder calculi, stomach calculi, but also be used to cut the pathological change tissues in the urinary system, such as congenital stricture of urethra, hypertrophic scar, etc.

According to an aspect of the present invention, there is provided a method for breaking up calculi in urinary intracavity by milling. The method comprises the steps of: inserting a combination of an endoscope, a driving assembly and a milling assembly or a combination of an endoscope with a sleeve, a driving assembly, and a milling assembly into the urinary intracavity; starting up a driving unit to drive the milling assembly so as to mill the calculi in the intracavity into powder; and discharging the milled calculi powder out of the body by a natural manner or by water flush and/or vacuum suction.

A calculi breakup apparatus is adopted in the method for breaking up calculi in the urinary intracavity by milling. The apparatus comprises an endoscope with its attachments, energy supply device and a control host. It is featured in that: the milling assembly is in cooperation with the endoscope with its attachments, one end of the milling assembly is connected to the driving unit mounted in the driving assembly, a control switch is connected to a control host. Once the control host provides energy supply (electrical supply or air supply), the driving unit starts to operate and the milling assembly rotates, so as to mill the calculi in urinary intracavity into powder and then discharge it out of the body. Therefore, lithotripsy effect, which is equal to or better than that of other calculi breakup apparatus, can be achieved.

The milling assembly comprises a transmission shaft, a sleeve, and a milling head and a supporter mounted on an end of the transmission shaft, wherein the transmission shaft is installed in the sleeve, a bearing is mounted near to the milling head and is located at a position between the transmission shaft and the sleeve, the sleeve is surrounded by a sleeve sheath connected with the driving assembly, the other end of the transmission shaft is connected to the driving unit by means of a key. Here, the supporting device functions to prevent the milling head from damaging the endoscope and allows flushing water to flow therethrough.

The milling head is made of material harder than the calculi such as diamond, hard alloy, corundum, and ceramic material. The milling head may have various shapes or have a bit structure.

The apparatus for breaking up calculi in the urinary intracavity by milling further comprises a subsidiary Y-shaped sleeve which may be inserted into the endoscope, wherein the Y-shaped sleeve has a slant end or a curved end, the Y-shaped sleeve has a branch opening communicated with a negative pressure unit, wherein the milled calculi powder is discharged from the branch opening of the Y-shaped sleeve.

The driving assembly comprises an endoscope bayonet, an outer support, a sliding bar, an inner support, a sleeve sheath locking member, a sleeve sheath abutting bar, a sensitive switch or pressure sensor, an abutting bar tension spring, a screw biasing force adjustor, wherein the endoscope bayonet is mounted outside the outer support to fix the endoscope, the inner support and the outer support are engaged with each other and adapted for mounting the snap spring, the abutting bar, an inner spring, the screw biasing force adjustor, the sensitive switch or pressure sensor, a driving unit and an outer spring; the snap spring is adapted for snap-coupling the milling assembly; the abutting bar is a component which controls the sensitive switch or the pressure sensor, wherein once the milling head abuts on the calculi, a thrust force is transmitted to the abutting bar, and the sensitive switch or the pressure sensor is triggered to operate; the inner spring and the screw biasing force adjustor are adapted for adjusting a thrust force of the abutting bar; and the outer spring is mounted between the outer support and the inner support, wherein the milling head is retracted into the endoscope when it is not required to be in an operation mode, and when it is in an operation mode, the inner support is manually pushed so that the milling head is pushed out of the endoscope to mill, grind, drill the calculi.

The driving assembly may be embodied in a pistol shape. An outer end of the inner support is formed as a trigger; or may be embodied as a pushrod.

The energy supply device may include electrical supply or air supply to provide the control host with a power source, and the driving unit is cooperated with the power source of the energy supply device, the driving unit is embodied as a motor when the energy supply is the electrical supply, and the driving unit is embodied as an air-operated turbine driven by compressed air when the energy supply is the air supply.

The control host comprises a sensitive switch or pressure sensor signal receiving device, a singlechip or control device, an energy output system and a speed adjusting switch, after the sensitive switch or pressure sensor mounted in the driving assembly is activated, a signal is transmitted to the receiving device and is processed by the single chip microcomputer, microcontroller unit or control device, and the electrical supply or air supply is outputted to the driving unit from the energy output system, so as to operate the milling head.

The apparatus for breaking up calculi in urinary intracavity by milling of the present invention takes the following operation principles and processes: firstly, inserting the endoscope into the urinary intracavity and looking for the calculi, pushing the inner support to extend the milling assembly out of the endoscope, manually starting up the control host and aligning the milling head with the calculi to mill the calculi at a high speed, or abutting the calculi by the milling head and triggering the sensitive switch or pressure sensor by the abutting bar to allow the control host and energy supply device system to operate automatically so that the milling head mills the calculi by aligning the milling head with the calculi. The milled calculi powder can be discharged by emiction or the milled calculi powder can be discharged through the branch opening of the Y-shaped sleeve outside the endoscope by connecting the lateral opening with the negative pressure unit.

Compared to the existing method and apparatus for electrohydraulic shockwave lithotripsy, pneumatic ballistic lithotripsy, laser lithotripsy, and ultrasonic lithotripsy, the present invention has the following advantages of:

1. In the apparatus for breaking up calculi in urinary intracavity by milling, the milling head is in direct contact with and breaks up the calculi by transmitting the mechanical energy directly without generating any heat to hurt the urinary system mucous membrane. The milling head breaks up calculi directly by mechanical energy, instead of laser and pulsed discharge. It also has great safety for both the doctor and the patient.

2. The milling velocity of the air-operated driving unit may reach 10000-600000 rpm and the milling velocity of the brushless electric motor can reach 5000-300000 rpm. With such high velocity, there achieves high calculi breakup efficiency. It is suitable for breaking up calculi in the intracavity, such as renal calculus, ureter calculus, bladder calculus, and urethra calculus.

3. Compared to other intracavity calculi breakup method, the present invention has the advantages of non-traumatic to the body tissue, painless, short time for the treatment, and low calculi residual rate. The milling assembly with which the calculi breakup apparatus breaks up calculi in urinary intracavity by milling is low in production cost so that it can be used only one time to prevent cross infection caused by bad sterilization. The milling assembly and a handle can be installed and removed quickly. The connection is simple and convenient. The apparatus can be conveniently maintained.

4. The present invention may be applied not only on the calculi breakup in urinary intracavity but also on the milling of hepatic and gallbladder calculi and stomach calculi, further, it may be used to cut the pathological change tissues in the urinary system, such as congenital stricture of urethra, hypertrophic scar, etc.

DETAILED DESCRIPTION OF PREFERRED EMBODIMENTS OF THE INVENTION

Figure 1:
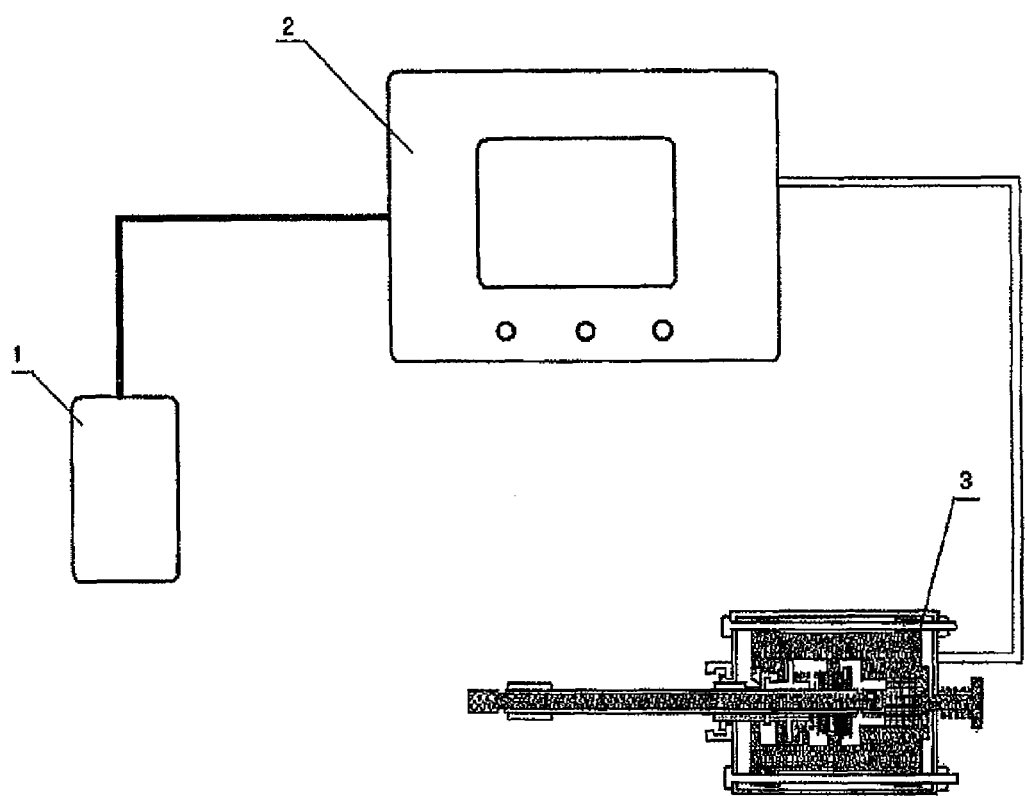
FIG. 1 is a schematic view of a whole apparatus for breaking up calculi in urinary intracavity by milling according to the present invention.

As shown in FIG. 1, an apparatus for breaking up calculi in urinary intracavity by milling according to the present invention comprises an energy supply device 1, a control host 2, and a driving assembly and a milling assembly 3. The energy supply device 1 is an electrical supply or an air supply adapted for providing power source to the control host 2. The control host 2 has a single chip microcomputer, microcontroller unit or a control device, a signal receiving device for a sensitive switch or pressure sensor 21, an energy output system and a speed adjusting switch accommodated therein and is used for controlling the driving assembly and the milling assembly 3.

Figure 2:
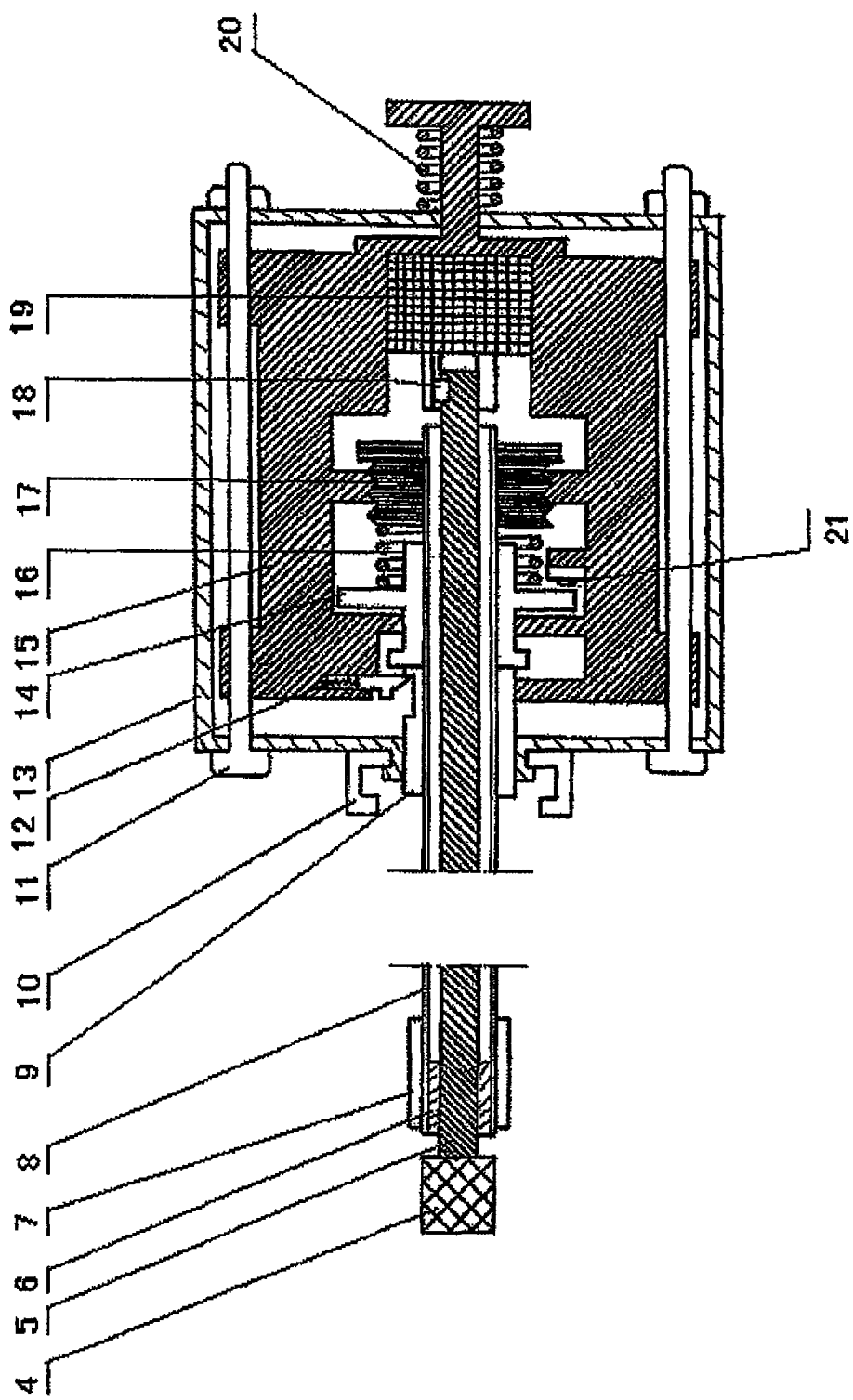
FIG. 2 is a view for a driving assembly and a milling assembly of the apparatus in an assembled state.

As shown in FIG. 2, the milling assembly comprises a milling head 4, a transmission shaft 5, a bearing 6, a supporter 7, a sleeve 8, and a sleeve sheath 9. The transmission shaft 5 is installed in the sleeve 8, a bearing 6 is mounted near to the milling head 4 and is located at a position between the transmission shaft 5 and the sleeve 8, the sleeve sheath 9 is fixed around the sleeve 8, the sleeve sheath 9 is connected with an outer support 13, a snap spring 12 and an abutting bar 14 of the driving assembly, and the other end of the transmission shaft 5 is connected to a driving unit 19 by means of a key 18. The supporter 7 functions to prevent the milling head from damaging an endoscope and can allow flushing water flow to pass therethrough. The driving assembly comprises an endoscope bayonet 10, the outer support 13, a sliding bar 11, an inner support 15, the snap spring 12, the abutting bar 14, a sensitive switch or pressure sensor 21, an inner spring 16, and an inner spring biasing force adjustor 17, the key 18, the driving unit 19, and an outer spring 20. The endoscope bayonet 10 is mounted outside the outer support 13 for fastening the endoscope thereon. The inner support 15 and the outer support 13 are cooperated with each other for mounting the snap spring 12, the abutting bar 14, the inner spring 16, the inner spring biasing force adjustor 17, the sensitive switch or pressure sensor 21, the driving unit 19 and the outer spring 20. The snap spring 12 is used for fastening the milling assembly. The milling assembly can be quickly taken out by moving the snap spring 12. The abutting bar 14 is an element used to manipulate the sensitive switch or pressure sensor 21. When the milling head 4 is abutted against the calculi, the thrust force is transmitted to the abutting bar 14. The sensitive switch or the pressure sensor 21 is triggered to operate; the inner spring 16 and the inner spring biasing force adjustor 17 are adapted for adjusting a thrust force of the abutting bar 14. The inner support 15 has a pushrod-shaped outer end.

The milling head 4 is made of diamond, hard alloy, corundum, and ceramic material, and it has a plurality of shapes such as cylindrical shape and conical shape, or has a bit structure.

Figure 3:
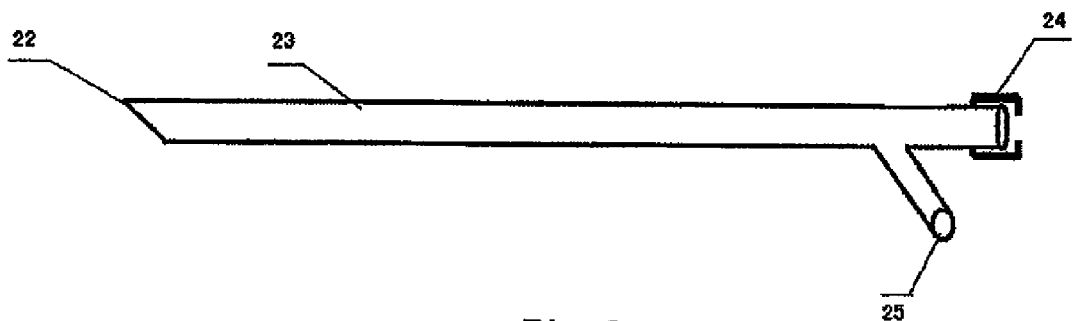
FIG. 3 is a structural schematic view of a subsidiary Y-shaped sleeve.

As shown in FIG. 3, a Y-shaped sleeve 23 comprises a slant opening or a curved opening 22, a waterproof glue cap 24, and a branch opening 25. When in operation, the endoscope is inserted into the Y-shaped sleeve 23 through the waterproof glue cap 24, the slant opening or curved opening 22 is abutted against the calculi, the milling head rotates at a high speed to break up the calculi, and the milled calculi is discharged through the branch opening 25 connected with a negative pressure suction unit.

Figure 4:
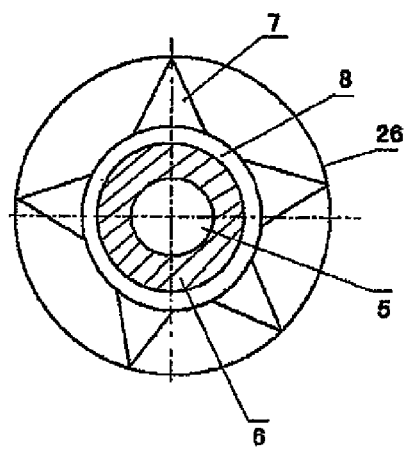
FIG. 4 is a perspective view illustrating a relationship between a support structure and a sleeve.

FIG. 4 illustrates a relationship between a support structure and a sleeve. In FIG. 4, there are an endoscope operating passage 26, the transmission shaft 5, the bearing 6, the supporter 7, and the sleeve 8. The transmission shaft 5 is installed in the sleeve 8, and the supporter 7 is mounted outside the sleeve 8 to just pass through the endoscope operating passage 26. With the support structure, a gap is formed through which water flow can pass during the operation, so as to flush the calculi to protect the endoscope from being worn by the milling head.

Effect of Specific Milling Operation

External Experimentations

First, to divide calculi from the body of a patient into two identical pieces by diamond-impregnated blade; through an 16F sleeve, to break up the calculi by the endoscope combined with the intracavity lithotripsy and then to pick it up through the sleeve. One piece is treated by a pneumatic ballistic lithotripsy device while the other piece is treated by the calculi breakup apparatus for breaking up calculi in urinary intracavity by milling according to the present invention. There are totally 30 examples. As a result, the velocity of the calculi breakup apparatus for breaking up calculi in urinary intracavity by milling according to the present invention is as twice as that of the pneumatic ballistic lithotripsy device.

What is claimed is:

1. A caculi breakup apparatus for breaking up calculi in urinary intracavity, the apparatus comprises:
    an endoscope,
    a driving assembly, and
    a milling assembly configured to be inserted into the urinary intracavity so as to mill the calculi in the intracavity into powder, thereby discharging the milled calculi powder out of the body, wherein the calculi breakup apparatus further comprises attachments of the endoscope, an energy supply device and a control host, wherein:
    the milling assembly is in cooperation with the endoscope with its attachments, one end of the milling assembly is connected to a driving unit mounted in the driving assembly, a sensitive switch or a pressure sensor is connected to the control host, said driving assembly comprises an endoscope bayonet, an outer support, a sliding bar, an inner support, a snap spring, an abutting bar, the sensitive switch or pressure sensor, an inner spring, and an inner spring biasing force adjuster, wherein the endoscope bayonet is mounted outside the outer support, the inner support and the outer support are cooperated with each other for mounting the snap spring, the abutting bar, the inner spring, the inner spring biasing force adjuster, the sensitive switch or pressure sensor, the driving unit and an outer spring, the inner spring and the inner spring biasing force adjuster are adapted for adjusting a thrust of the abutting bar; and the outer spring is mounted between the outer support and the inner support.

2. The calculi breakup apparatus according to claim 1, characterized in that:
    said milling assembly comprises a transmission shaft, a sleeve, a milling head mounted on an end of the transmission shaft, and a supporter, wherein the transmission shaft is installed in the sleeve, a bearing is mounted near to the milling head and is located at a position between the transmission shaft and the sleeve, a sleeve sheath is fastened outside the sleeve and connected with the driving assembly, the other end of the transmission shaft is connected to the driving unit by means of a key.

3. The calculi breakup apparatus according to claim 2, characterized in that:
    said milling head is made of diamond, hard alloy, corundum, or ceramic material and has a plurality of shapes or has a bit structure.

4. The calculi breakup apparatus according to claim 1, characterized in that:
    the apparatus further comprises a subsidiary Y-shaped sleeve inserted into the endoscope, the Y-shaped sleeve has a slant opening or a curved opening, the Y-shaped sleeve has a branch opening communicated with a negative pressure unit, wherein the milled calculi powder is discharged from the branch opening of the Y-shaped sleeve.

5. The calculi breakup apparatus according to claim 1, characterized in that:
    said energy supply device is an electrical supply or air supply to provide a power source to the control host, and the driving unit is cooperated with the power source of the energy supply device, the driving unit is a motor when the energy supply device is the electrical supply, and the driving unit is an air-operated turbomachine driven by compressed air when the energy supply device is an air supply.

6. The calculi breakup apparatus according to claim 1, characterized in that:
    said control host comprises a sensitive switch or pressure sensor signal receiving device, a single chip microcomputer or microcontroller unit or control device, an energy output system and a speed adjusting switch, wherein after the sensitive switch or pressure sensor mounted in the driving assembly is activated, a signal is transmitted to the receiving device and is processed by the single chip microcomputer or microcontroller unit or control device, and an electrical supply or air supply is outputted to the driving unit from the energy output system, so as to operate the milling head.

7. The calculi breakup apparatus according to claim 1, characterized in that:
    a velocity of milling is 10000-500000 rpm when the driving unit is an air-operated turbomachine; and the velocity of milling is 5000-300000 rpm when the driving unit is a brushless motor.

* * * * *

UNITED STATES PATENT AND TRADEMARK OFFICE
CERTIFICATE OF CORRECTION

PATENT NO.       : 8,562,625 B2                                                                 Page 1 of 1
APPLICATION NO. : 13/122609
DATED            : October 22, 2013
INVENTOR(S)      : Qiwu Ding It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 203 days.

Signed and Sealed this

Fifteenth Day of September, 2015

Michelle K. Lee
*Director of the United States Patent and Trademark Office*